(12) United States Patent
Gifford, III et al.

(10) Patent No.: US 11,504,237 B2
(45) Date of Patent: Nov. 22, 2022

(54) CARDIAC VALVE REPAIR DEVICES WITH ANNULOPLASTY FEATURES AND ASSOCIATED SYSTEMS AND METHODS

(71) Applicant: Half Moon Medical, Inc., Menlo Park, CA (US)

(72) Inventors: Hanson S. Gifford, III, Woodside, CA (US); Matthew McLean, San Francisco, CA (US); Gaurav Krishnamurthy, Mountain View, CA (US); Neil Zimmerman, Menlo Park, CA (US)

(73) Assignee: Half Moon Medical, Inc., Menlo Park, CA (US)

( * ) Notice: Subject to any disclaimer, the term of this patent is extended or adjusted under 35 U.S.C. 154(b) by 0 days.

(21) Appl. No.: 16/817,464

(22) Filed: Mar. 12, 2020

(65) Prior Publication Data
US 2020/0289265 A1     Sep. 17, 2020

Related U.S. Application Data

(60) Provisional application No. 62/817,443, filed on Mar. 12, 2019.

(51) Int. Cl.
*A61F 2/24*         (2006.01)

(52) U.S. Cl.
CPC .......... *A61F 2/2448* (2013.01); *A61F 2/2418* (2013.01); *A61F 2/2442* (2013.01); *A61F 2220/0016* (2013.01); *A61F 2250/001* (2013.01)

(58) Field of Classification Search
None
See application file for complete search history.

(56) References Cited

U.S. PATENT DOCUMENTS

| 6,869,444 B2 | 3/2005 | Gabbay |
| 7,160,322 B2 | 1/2007 | Gabbay |

(Continued)

FOREIGN PATENT DOCUMENTS

| EP | 2819618 A1 | 1/2015 |
| EP | 3167846 A1 | 5/2017 |

(Continued)

OTHER PUBLICATIONS

ISA, PCT Application No. PCTUS2018/061126, International Search Report and Written Opinion dated Jul. 9, 2019, 12 pages.

(Continued)

*Primary Examiner* — Leslie Lopez
(74) *Attorney, Agent, or Firm* — Perkins Coie LLP

(57) ABSTRACT

Cardiac valve repair devices with annuloplasty features and associated systems and methods are disclosed herein. A cardiac valve repair device configured in accordance with embodiments of the present technology can include, for example, an atrial fixation member configured to engage tissue within a left atrium proximate to a native mitral valve and a spring mechanism coupled to an inferior edge portion of the atrial fixation member. The spring mechanism has an extended state with a first length corresponding to a dimension of the atrial fixation member in a deployed state and a relaxed state with a shorter length corresponding to a desired dimension of the native valve annulus. When implanted, the spring mechanism contracts the atrial fixation member such that the native mitral annulus anchored to the atrial fixation member reduces in a cross-sectional dimension.

28 Claims, 7 Drawing Sheets

(56) References Cited

U.S. PATENT DOCUMENTS

| | | | |
|---|---|---|---|
| 9,011,523 B2 | 4/2015 | Sequin | |
| 9,592,118 B2 | 3/2017 | Khairkhahan et al. | |
| 9,592,121 B1 | 3/2017 | Khairkhahan | |
| 9,610,163 B2 | 4/2017 | Khairkhahan et al. | |
| 9,907,652 B2 | 3/2018 | Chau et al. | |
| 10,123,874 B2 | 11/2018 | Khairkhahan et al. | |
| 10,166,098 B2 | 1/2019 | Khairkhahan et al. | |
| 10,390,714 B2 | 8/2019 | Wolinsky et al. | |
| 10,449,046 B2 | 10/2019 | Rafiee | |
| 10,470,883 B2 | 11/2019 | Khairkhahan et al. | |
| 10,478,303 B2 | 11/2019 | Khairkhahan | |
| 10,500,048 B2 | 12/2019 | Khairkhahan et al. | |
| 10,512,542 B2 | 12/2019 | Khairkhahan et al. | |
| 10,702,386 B2 | 7/2020 | Khairkhahan et al. | |
| 11,000,372 B2 | 5/2021 | Khairkhahan et al. | |
| 11,083,572 B2 | 8/2021 | McLean et al. | |
| 11,344,410 B2 | 5/2022 | Hacohen et al. | |
| 2003/0199975 A1 | 10/2003 | Gabbay | |
| 2004/0093060 A1* | 5/2004 | Seguin | A61F 2/2418 623/1.11 |
| 2007/0038297 A1 | 2/2007 | Bobo, Jr. et al. | |
| 2008/0077235 A1* | 3/2008 | Kirson | A61F 2/2409 623/2.11 |
| 2010/0217382 A1 | 8/2010 | Chau et al. | |
| 2010/0262233 A1 | 10/2010 | He | |
| 2010/0280604 A1 | 11/2010 | Zipory et al. | |
| 2011/0029072 A1 | 2/2011 | Gabbay | |
| 2011/0276130 A1 | 11/2011 | Alameddine | |
| 2012/0197388 A1* | 8/2012 | Khairkhahan | A61B 17/068 623/2.11 |
| 2012/0197392 A1 | 8/2012 | DuMontelle et al. | |
| 2013/0006352 A1 | 1/2013 | Yaron | |
| 2014/0067048 A1 | 3/2014 | Chau et al. | |
| 2014/0358223 A1 | 12/2014 | Rafiee et al. | |
| 2015/0142104 A1 | 5/2015 | Braido | |
| 2015/0148893 A1 | 5/2015 | Braido et al. | |
| 2015/0230919 A1 | 8/2015 | Chau et al. | |
| 2015/0327996 A1* | 11/2015 | Fahim | A61F 2/844 623/2.17 |
| 2016/0030176 A1 | 2/2016 | Mohl et al. | |
| 2016/0045165 A1 | 2/2016 | Braido et al. | |
| 2016/0045316 A1 | 2/2016 | Braido et al. | |
| 2016/0074164 A1* | 3/2016 | Naor | A61F 2/2418 623/2.11 |
| 2017/0065418 A1 | 3/2017 | Skarsgard | |
| 2017/0095332 A1 | 4/2017 | Bruchman | |
| 2017/0165067 A1 | 6/2017 | Barajas-Torres et al. | |
| 2017/0258589 A1 | 9/2017 | Pham et al. | |
| 2017/0296706 A1* | 10/2017 | Simon | B01D 61/28 |
| 2018/0143087 A1 | 5/2018 | Gouko et al. | |
| 2018/0147054 A1 | 5/2018 | Chau et al. | |
| 2018/0243087 A1 | 8/2018 | Kapadia | |
| 2018/0271651 A1 | 9/2018 | Christianson et al. | |
| 2018/0325666 A1 | 11/2018 | Ma | |
| 2019/0091047 A1 | 3/2019 | Walsh | |
| 2020/0188108 A1* | 6/2020 | Grimm | A61F 2/2445 |
| 2020/0205978 A1 | 7/2020 | Padala et al. | |
| 2020/0222185 A1 | 7/2020 | Kappetein et al. | |
| 2020/0268512 A1 | 8/2020 | Mohl | |
| 2020/0360138 A1 | 11/2020 | Ma | |
| 2021/0085462 A1 | 3/2021 | Gifford, III et al. | |
| 2021/0307901 A1 | 10/2021 | Rannani | |
| 2022/0039951 A1 | 2/2022 | Khairkhahan et al. | |
| 2022/0125579 A1 | 4/2022 | McLean et al. | |
| 2022/0125586 A1 | 4/2022 | Rafiee | |
| 2022/0160508 A1 | 5/2022 | Miyashiro et al. | |

FOREIGN PATENT DOCUMENTS

| | | |
|---|---|---|
| WO | 2005002424 A3 | 1/2005 |
| WO | 2012177942 A2 | 12/2012 |
| WO | 2014195422 A1 | 12/2014 |
| WO | 2014207575 A2 | 12/2014 |
| WO | 2018142186 A1 | 8/2018 |
| WO | 2019045910 A1 | 3/2019 |
| WO | 2020101676 A1 | 5/2020 |

OTHER PUBLICATIONS

ISA, PCT Application No. PCT/US2020/013953, International Search Report and Written Opinion dated Apr. 15, 2020, 14 pages.

ISA, PCT Application No. PCT/US2020/022471, International Search Report and Written Opinion dated Jun. 3, 2020, 17 pages.

ISA, PCT Application No. PCT/US2020/051887, International Search Report and Written Opinion dated Nov. 27, 2020, 13 pages.

* cited by examiner

CARDIAC VALVE REPAIR DEVICES WITH ANNULOPLASTY FEATURES AND ASSOCIATED SYSTEMS AND METHODS

CROSS-REFERENCE TO RELATED APPLICATION(S)

This application claims priority to and the benefit of U.S. Provisional Application No. 62/817,443, filed Mar. 12, 2019, which is incorporated herein by reference in its entirety.

TECHNICAL FIELD

The present technology is directed to cardiac valve repair devices, and more particularly to cardiac valve repair devices with annuloplasty features and associated systems and methods.

BACKGROUND

Conditions affecting the proper functioning of the mitral valve include, for example, mitral valve regurgitation, mitral valve prolapse and mitral valve stenosis. Mitral valve regurgitation is a disorder of the heart in which the leaflets of the mitral valve fail to coapt into apposition at peak contraction pressures, resulting in abnormal leaking of blood from the left ventricle into the left atrium. There are several structural factors that may affect the proper closure of the mitral valve leaflets. For example, many patients suffering from heart disease have an enlarged mitral annulus caused by dilation of heart muscle. Enlargement of the mitral annulus makes it difficult for the leaflets to coapt during systole. A stretch or tear in the chordae tendineae, the tendons connecting the papillary muscles to the inferior side of the mitral valve leaflets, may also affect proper closure of the mitral annulus. A ruptured chordae tendineae, for example, may cause a valve leaflet to prolapse into the left atrium due to inadequate tension on the leaflet. Abnormal backflow can also occur when the functioning of the papillary muscles is compromised, for example, due to ischemia. As the left ventricle contracts during systole, the affected papillary muscles do not contract sufficiently to effect proper closure.

Mitral valve prolapse, or when the mitral leaflets bulge abnormally up in to the left atrium, causes irregular behavior of the mitral valve and may also lead to mitral valve regurgitation. Normal functioning of the mitral valve may also be affected by mitral valve stenosis, or a narrowing of the mitral valve orifice, which causes impedance of filling of the left ventricle in diastole.

Mitral valve regurgitation is often treated using diuretics and/or vasodilators to reduce the amount of blood flowing back into the left atrium. Other treatment methods, such as surgical approaches (open and intravascular), have also been used for either the repair or replacement of the valve. For example, repair procedures include resecting portions of the dilated annulus and suturing or clipping of the valve leaflets into partial apposition with one another.

In some patients, the native mitral leaflets are still intact and healthy, but dilation of the annulus prevents the leaflets from coaptation in systole, resulting in regurgitation. These patients may benefit from an annuloplasty device and method, which includes the implantation of annular or peri-annular rings that are secured to the annulus or surrounding tissue and cinches the annulus. Such an annuloplasty would effectively reduce the size of native mitral annulus, thereby moving the native leaflets closer together again and allowing the native leaflets (or a portion thereof) to coapt during systole.

In patients with mitral valve regurgitation caused in part by factors beyond annulus dilation, procedures can be used to address a significant portion of the mitral regurgitation. For instance, placing a clip (e.g., a Mitra-clip manufactured by Abbott Labs) might address a flail leaflet due to a ruptured chordae tendinea. In addition, more invasive procedures involve the replacement of the entire valve itself where mechanical valves or biological tissue are implanted into the heart in place of the mitral valve. These invasive procedures are conventionally done through large open thoracotomies and are thus very painful, have significant morbidity, and require long recovery periods. Even with these procedures, an uncorrected a dilated native annulus may result in an imperfect repair of the valve that does not eliminate mitral regurgitation. In these cases, a device and method for concomitant annuloplasty is expected to enhance mitral valve repair.

With many of these mitral valve repair and replacement procedures, the durability of the devices or improper sizing of annuloplasty rings or replacement valves may result in additional problems for the patient. Moreover, many of the repair procedures are highly dependent upon the skill of the cardiac surgeon where poorly or inaccurately placed sutures may affect the success of procedures.

Further complicating the mitral valve repair and replacement procedures is the fact that, compared to other cardiac valves (e.g., the aortic valve), the mitral valve annulus has limited radial support from surrounding tissue and the mitral valve has an irregular, unpredictable shape. For example, the inner wall of the mitral valve is bound by only a thin vessel wall separating the mitral valve annulus from the inferior portion of the aortic outflow tract. As a result, significant radial forces on the mitral annulus could lead to collapse of the inferior portion of the aortic tract with potentially fatal consequences. The chordae tendineae of the left ventricle are often an obstacle in deploying a mitral valve repair device. The maze of chordae in the left ventricle makes navigating and positioning a deployment catheter that much more difficult in mitral valve repair. Given the difficulties associated with current procedures, there remains the need for simple, effective, and less invasive devices and methods for treating dysfunctional heart valves.

BRIEF DESCRIPTION OF THE DRAWINGS

Many aspects of the present disclosure can be better understood with reference to the following drawings. The components in the drawings are not necessarily to scale, and instead emphasis is placed on illustrating clearly the principles of the present disclosure. For ease of reference, throughout this disclosure identical reference numbers and/ or letters are used to identify similar or analogous components or features, but the use of the same reference number does not imply that the parts should be construed to be identical. Indeed, in many examples described herein, identically numbered components refer to different embodiments that are distinct in structure and/or function. The headings provided herein are for convenience only.

DETAILED DESCRIPTION

Figure 1A:
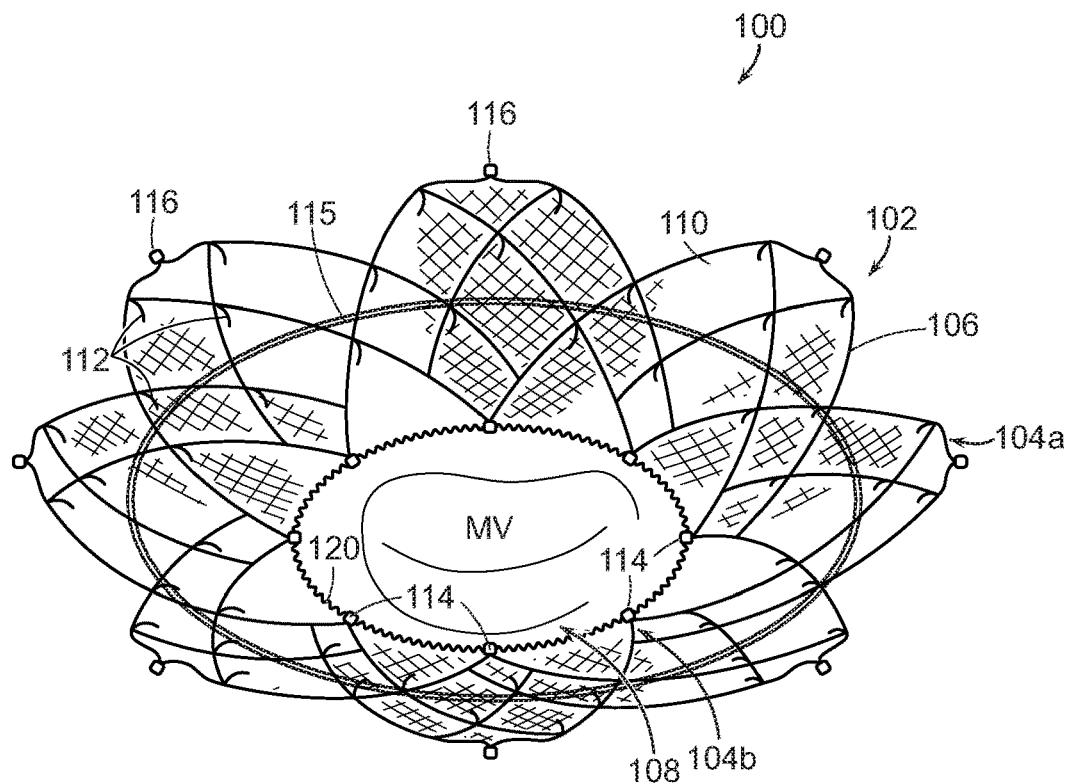
FIGS. 1A and 1B are isometric views of a mitral valve repair device configured in accordance with embodiments of the present technology.

Cardiac valve repair devices with annuloplasty features and associated systems and methods are disclosed herein. In some embodiments, for example, a cardiac valve repair device (also referred to as an "annuloplasty device," a "mitral valve repair device," or a "coaptation assist device") includes a fixation member that anchors to cardiac tissue of the left atrium that surrounds the mitral annulus and spring features that draw the native annulus inward to allow the valve leaflets (or portions thereof) to once again coapt during systole. Specific details of several embodiments of the technology are described below with reference to FIGS. 1A-7. Although many of the embodiments are described below with respect to implant devices, systems, and methods for repair of a native mitral valve, other applications and other embodiments in addition to those described herein are within the scope of the technology. For example, the present technology may be used at other target sites, like the tricuspid valve, the pulmonary valve, and/or the aortic valve. Additionally, several other embodiments of the technology can have different configurations, components, or procedures than those described herein, and features of the embodiments shown can be combined with one another. A person of ordinary skill in the art, therefore, will accordingly understand that the technology can have other embodiments with additional elements, or the technology can have other embodiments without several of the features shown and described below with reference to FIGS. 1A-7.

With regard to the terms "distal" and "proximal" within this description, unless otherwise specified, the terms can reference a relative position of the portions of a valve repair device and/or an associated delivery device with reference to an operator and/or a location in the vasculature or heart. For example, in referring to a delivery catheter suitable to deliver and position various valve repair devices described herein, "proximal" can refer to a position closer to the operator of the device or an incision into the vasculature, and "distal" can refer to a position that is more distant from the operator of the device or further from the incision along the vasculature (e.g., the end of the catheter). With respect to a heart valve repair device, the terms "proximal" and "distal" can refer to portions of the device relative to the native annulus. For example, "proximal" can refer to an upstream portion of the device spaced apart from the native annulus, and "distal" can refer to a downstream position at or proximate to the native annulus.

Overview

The present technology includes minimally-invasive devices and methods for reducing the annular circumference of an atrioventricular valve. Embodiments of the mitral valve repair devices with annuloplasty features disclosed herein include an anchoring member (also referred to as a "fixation member" or "brim") placed in the atrium of the heart, against the atrial walls just above the atrioventricular valve. The anchoring member can be sized and shaped to conform to the walls of the left atrium just above the mitral annulus. In various embodiments, the anchoring member has cleats or other frictional elements to hold it in place against the atrial wall. Over a period after implantation (e.g., 3 days, 2 weeks, 1 month, 2 months, 3 months), the anchoring member or portions thereof become covered by a layer of tissue, and this tissue ingrowth adheres it permanently to the atrial wall. During this recovery period, the anchoring member heals into the walls of the atrium (e.g., four to twelve weeks), at which point the anchoring member itself can begin to shrink in circumference, thereby reducing the circumference of the valve annulus. The annuloplasty device may be designed to be placed in the mitral valve and/or the tricuspid valve and can be delivered into the left atrium via a trans-septal (trans-venous) approach. In some embodiments, the annuloplasty device can be configured to be placed at the site of other native valves, such as the aortic valve.

In some embodiments, the device is designed to differentially shrink certain areas of the annulus. For example, the device can be configured to more aggressively shrink the lateral and medial portions of the mitral annulus near the commissures and the P1 and P3 segments of the posterior leaflet (i.e., the medial and lateral portions of the posterior leaflet), pulling the posterior leaflet closer to the anterior leaflet. In the tricuspid valve, the device may be configured to more aggressively shrink the free wall in the areas of the anterior and posterior leaflets.

The device can be designed to reduce the annular circumference to a very specific smaller dimension. In other embodiments, the device can be configured to apply an elastic reducing force to annulus over a range of diameters, thereby reducing the maximum force applied to the annulus at any specific point in time.

In some embodiments, the device includes an anchoring member and one or more fixation members (e.g., screws) that fixate the device to native tissue at or proximate to the annulus to provide traditional annuloplasty cinching. In these embodiments, the anchoring member and/or features coupled thereto may also address other issues with the valve leaflets that might be causing regurgitation. The anchoring member can be similar to the atrial fixation member (also referred to as a "brim") disclosed in International Patent Application No. PCT/US2018/043566, filed Jul. 24, 2018, which is incorporated by reference herein in its entirety. In various embodiments, the anchoring member is omitted such that the device includes one or more fixation members to provide a pure annuloplasty device.

The device may have various different cross-sectional shapes. In some embodiments, for example, the device is symmetrical and/or has a uniform cross-sectional shape, so that there is no need to orient the device relative to the anterior and posterior leaflets. In other embodiments, the device has a specific asymmetrical or non-uniform shape to align with one or more anatomic landmarks, such as the posterior leaflet and/or portions thereof. As an example, the asymmetrical device may have an overall shape that aligns with the general "D-shape" of the mitral annulus and/or the fixation member can have a saddle-like shape similar to the native mitral annulus to enhance coaptation geometry of the native leaflets. In certain embodiments, the fixation member may be shaped similar to surgical saddle shaped rings, such as the Profile 3D Annuloplasty System manufactured by Medtronic.

In some embodiments, the device may be configured such that the fixation member lays flat or substantially flat against the walls of the atrium, which typically have different slopes relative to the valve axis at different locations around the valve. In various embodiments, for example, the fixation member may have a specific shape that at least generally aligns with the native atrial wall structure surrounding the mitral valve. In various embodiments, the fixation member may be sufficiently flexible to conform to the variations in the native anatomy of the atrial walls. In various embodiments, the anchoring member may include portions that press against and anchor to sub-annular tissue.

In some embodiments, the device may be shaped to accommodate additional or other anatomical features of the atrium and/or other surrounding anatomy. For example, when configured for annuloplasty of the mitral valve, the device may be shaped to avoid pulmonary veins and/or the left atrial appendage. When the device is configured for implantation in the right portion of the heart, the device can be sized and shaped to avoid the coronary sinus and/or the inferior vena cava ("IVC"). In some embodiments, the device may be sized and shaped to partially or fully occlude the left atrial appendage to reduce or minimize the risk of thromboembolic stroke in patients with atrial fibrillation.

In some embodiments, the mitral valve repair devices can further include a coaptation structure (also referred to as a "baffle") extending from the anchoring member, through the annulus such that the coaptation structure is positioned over a portion of a native valve leaflet. The coaptation structure fills at least a portion of the space taken by the closed native leaflet and extends beyond that space to re-establish coaptation with the surrounding leaflets. For example, the coaptation structure may extend in front of a central portion of the posterior leaflet (i.e., P2 of the posterior leaflet), pushing the posterior leaflet back toward the ventricular wall, such that the coaptation structure is positioned to coapt with the anterior leaflet during systole. In some embodiments, the device further includes one or more clips that extend from the anchoring member and/or the coaptation structure to a position behind individual mitral valve leaflets to the sub-annular space for further stabilization of the implant. For example, the device can include a clip that reaches under the P2 or other portion of the posterior leaflet up to the sub-annular space and further stabilizes the implant. Further descriptions of implant devices with coaptation assist devices are also described in International Patent Application No. PCT/US2018/043566, filed Jul. 24, 2018, and in International Patent Application No. PCT/US2018/061126, filed Nov. 14, 2018, each of which is incorporated by reference in its entirety.

Selected Embodiments of Mitral Repair Devices with Annuloplasty Features

Figure 1B:
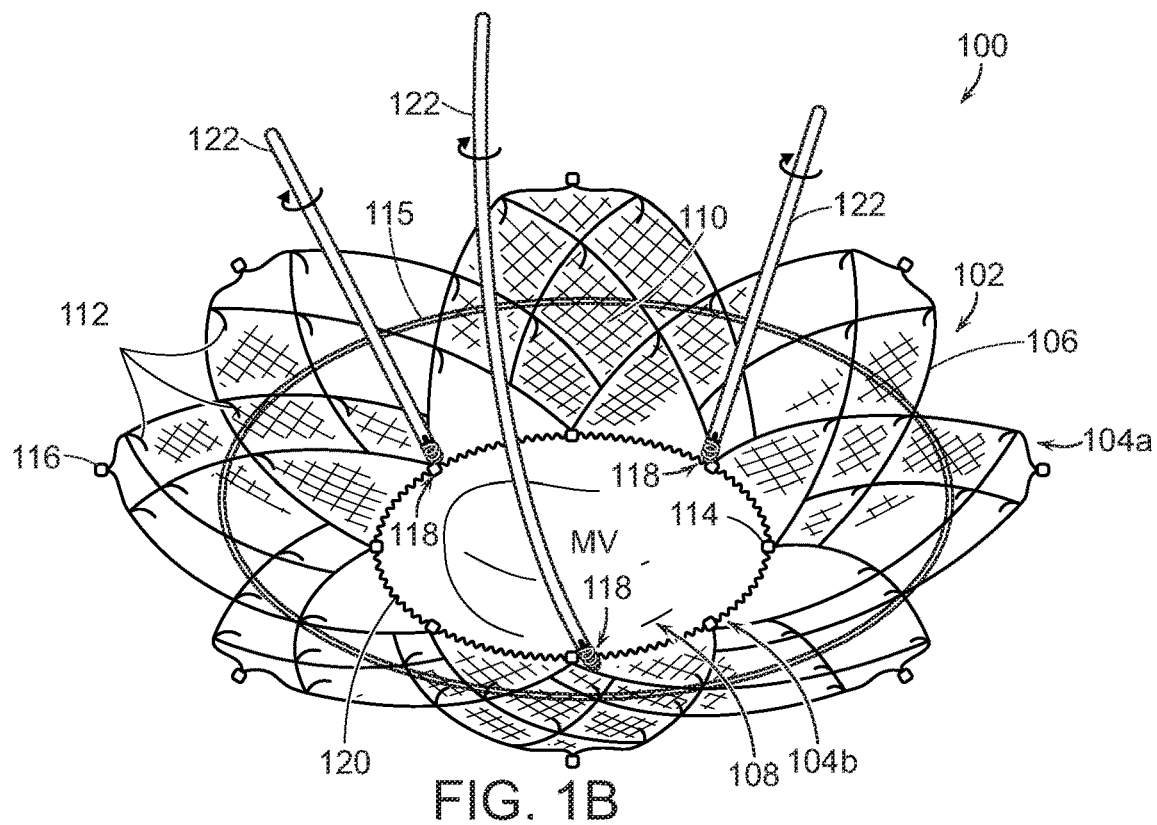
Figure 1C:
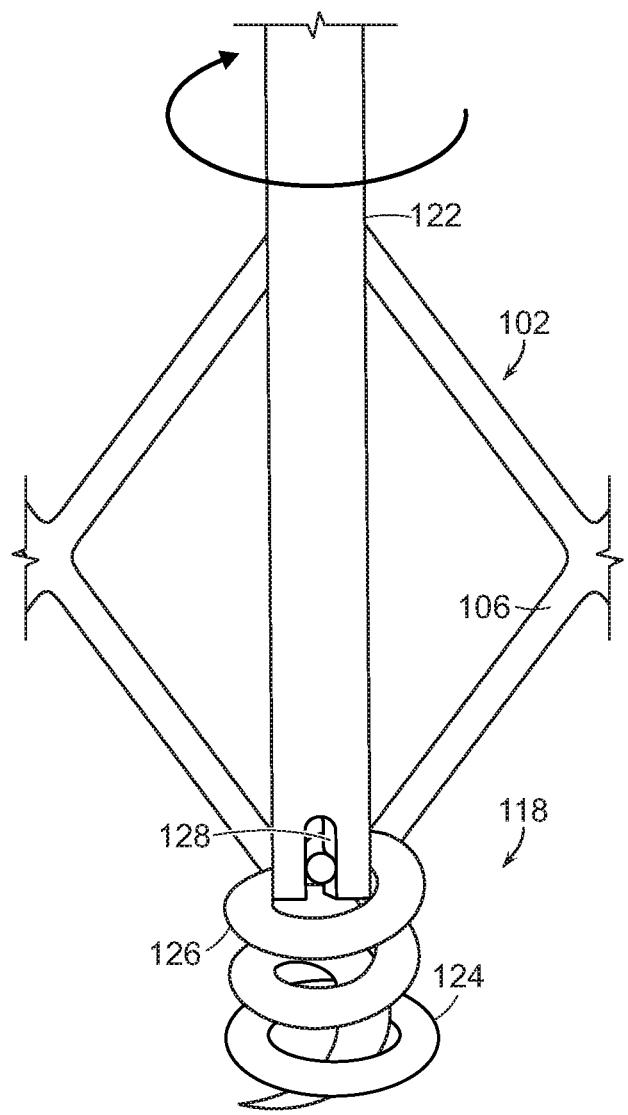
FIG. 1C is an enlarged view of a tissue anchoring element of a mitral valve repair device configured in accordance with embodiments of the present technology.

FIGS. 1A and 1B are isometric views of a cardiac valve repair device 100 (also referred to as "device 100") configured in accordance with embodiments of the present technology, and FIG. 1C is an enlarged view of tissue anchor portions of the device 100 configured in accordance with embodiments of the present technology. The device 100 includes an atrial fixation member 102 (also referred to as an "anchoring member 102" or "fixation member 102") shaped to engage and heal into the atrial wall of a patient just above an atrioventricular valve (e.g., the mitral valve MV or the tricuspid valve) and one or more tensile spring mechanisms 120 (also referred to as "spring elements") acting thereon to contract the dimensions of the fixation member 102. The fixation member 102 may be a self-expanding frame structure that naturally expands to a size slightly larger than the existing atrial dimensions. The fixation member 102 has a superior edge portion 104a (also referred to as "proximal edge portion 104a" and a "first edge portion 104a") configured to be positioned in an atrial region of the heart spaced apart from the native valve annulus and an inferior edge portion 104b (also referred to as "distal edge portion 104b" and a "second edge portion 104b") configured to be positioned at or adjacent to the native valve annulus. The spring mechanism 120 can be disposed at the inferior edge portion 104b. In the embodiment illustrated in FIG. 1A, for example, the spring mechanism 120 encircles the peripheral edge or perimeter of the inferior portion 104b of the fixation member 102. The spring mechanism 120 may also or alternatively be disposed differently along the inferior edge portion 104b, and/or the device 100 may include one or more spring mechanisms 120 along additional portions of the fixation member 102. For example, the spring mechanism 120 can include one or more spring components along the wall of the fixation member 102 between the superior and inferior edge portions 104a-b. After device implantation, the spring mechanism 120 is configured to contract, drawing in the adjoining portion of the fixation member 102 and the annular tissue attached thereto, and thereby reducing the dimensions of the annulus. This spring contraction can occur immediately after the fixation member is implanted and/or starting at a delayed time point after the fixation member 102 has healed into or affixed to the adjacent cardiac wall.

The fixation member 102 can include an expandable mesh frame 106 (e.g., a stent) having an oval, circular, or D-like cross-sectional shape in the deployed state and defining an open central lumen 108 (also referred to as the "opening 108") that allows blood to pass therethrough. The mesh frame 106 can be a stent made of nitinol or other suitable stent material (e.g., cut from a tube or flat sheet and formed into the above-described shape(s)). The fixation member 102 can be shaped to conform to the walls of the left atrium just above the mitral annulus to secure the device 100 to the supra-annular tissue. After implantation (e.g., 3 days, 2 weeks, 1 month, 2 months), the fixation member 102 or portions thereof become covered by a layer of tissue, and this tissue ingrowth adheres the device 100 permanently to the atrial wall. In some embodiments, the fixation member 102 includes a covering 110 made of fabric or tissue extending over at least a portion of the mesh frame 106 to enhance ingrowth and long-term integration with the atrial wall. In this and other embodiments, the mesh frame 106 of the fixation member 102 can be coated with or otherwise include a nitride-based nanomatrix (surface nitriding) to promote tissue ingrowth. In some embodiments, the fixation member 102 has a semi-circular or other shape that does not extend fully around the circumference of the native valve. In some embodiments, the fixation member 102 may also or alternatively include one or more portions that press against sub-annular tissue to provide sub-annular device fixation.

As shown in FIG. 1A, the device 100 can further include multiple barbs or cleats 112 disposed on the fixation member 102 to enhance immediate fixation, intermediate-term ingrowth, and long-term integration with the tissue of the atrial wall to facilitate tissue fixation that allows for effective application of force that reduces annular dimensions. These cleats 112 can be angled in one or more directions. For example, the cleats 112 can project outwardly in a distal direction towards the native valve annulus, so that tension applied by the fixation member 102 to shrink the native annulus tends to drive these cleats deeper into the tissue rather than pulling them out. In some embodiments, the cleats 112 may extend in a proximal direction away from the native valve annulus, point directly radially outward from their attachment points on the fixation member 102, curve inwardly toward the central longitudinal axis of the device 100, and/or otherwise extend from the fixation member 102 to engage native tissue and facilitate tissue fixation.

As further shown in FIG. 1A, the fixation member 102 can include delivery attachment features 116 positioned along the superior edge portion 104a to facilitate connection to a delivery device (not shown). In this and other embodiments, the device 100 can include attachment features 116 along an inferior edge portion 104b and/or along other portions of the fixation member 102. The attachment features 116 can include T-bars, eyelets, hooks, and/or other structures that can be secured to recesses, protrusions, grasping mechanisms, sutures, and/or other corresponding portions of the delivery system.

In some embodiments, the device 100 can include one or more suture rings 115 (also known as tensioning rings) that extend around a circumference of the fixation member 102. The suture rings 115 can be tensioned via the delivery system (not shown). For example, the suture rings 115 can include or be coupled to sutures or other elongated members that extend through the delivery catheter to an exit port outside of the body where they can be pulled to tighten the suture ring 115. Tensioning the suture ring 115 in this manner can position the fixation member 102 in a partially constrained state in which the fixation member 102 has a reduced diameter in comparison to a fully-expanded, free state. This constrained state can facilitate repositioning or retrieval of the device 100 during the delivery procedure. In some embodiments, the suture ring 115 can be tensioned after the delivery procedure. For example, the elongated members coupled to the suture ring 115 may extend through an access port (e.g., proximate to a patient's jugular or femoral vein) such that the elongated members are accessible post-delivery procedure. At some point after the delivery procedure, such as after tissue ingrowth has enhanced fixation of the fixation member 102 to the tissue surrounding the native annulus (e.g., about 3 months post-procedure), the elongated members can be pulled to cinch the suture ring 115 around the fixation member 102 and decrease the overall cross-sectional area of the device 100. Because the fixation member 102 is affixed to the tissue at the annulus, the tensioning of the suture ring 115 can also draw in the native annulus to decrease the overall size of the native annulus.

In some embodiments, the fixation member 102 can have a differential stent shape, dimensions, and/or thickness in specific regions of the fixation member 102. For example, the fixation member 102 can include additional cleats, barbs, or stent structure in areas of the fixation member 102 configured to be positioned near the fibrous trigones. These additional structures may enhance the ability of the device 100 to apply force to the annulus to reduce the anterior-posterior dimension.

As shown in FIG. 1B and the enlarged view of FIG. 1C, in some embodiments the device 100 further includes one or more anchoring elements 118 that are actuated after the fixation member 102 has been positioned against the atrial wall. The anchoring elements 118 can be captive in eyelets 124 (FIG. 1C) and/or other engagement structures on the distal edge portion 104b of the fixation member 102 closest to the atrioventricular valve. These anchoring elements 118 can be positioned at every node of the fixation member stent or at specific locations along the stent circumference. In the embodiment illustrated in FIG. 1B, for example, the anchoring elements 118 are positioned at three locations on the fixation member 102 configured to align with the trigones and the P2 region (central region) of the annulus. In other embodiments, the anchoring elements 118 are positioned elsewhere along the distal edge portion 104b of the fixation member 102 and/or the device 100 can include more than three or fewer than three anchoring elements 118.

In the illustrated embodiment, the anchoring elements 118 are helical coil anchors 126 (FIG. 1C) that extend through eyelets 124 of the fixation member 102. During device deployment, the helical coil anchors 126 are releasably coupled to a torqueable shaft 122, and rotation of the shaft 122 drives the coil anchor 126 into cardiac tissue at or proximate to the native annulus. As shown in FIG. 1C, the torqueable shaft 122 can have a groove 128 that receives a portion of the coil anchor 126 to allow the shaft 122 to impart rotation and/or downward force on the coil anchor 126 such that it engages the adjacent tissue. In these and other embodiments, the torqueable shaft 122 may be releasably attached to the anchoring element 118 using other suitable coupling mechanisms. In these and other embodiments, the anchoring elements 118 may have other structures suitable for anchoring the fixation member 102 into surrounding tissue and/or may be deployed via other mechanisms including self-deployment. In some embodiments, the anchoring elements 118 can be coated with PLGA and/or other coating materials to facilitate accelerated incorporation into surrounding tissue.

Referring back to FIG. 1A, the spring mechanism 120 may include one or more springs formed into a partial or full loop that is attached at several points around the circumference of the fixation member 102. When the spring mechanism 120 is attached around the distal edge portion of the fixation member 102 (as shown in FIGS. 1A and 1B), the spring mechanism 120 extends around the native annulus when the device 100 is implanted. The spring mechanism 120 may include one or more a coil springs, such as the springs used on guidewires or neurovascular embolic coils. In some embodiments, the spring mechanism 120 may be close-wound, so that it controllably contracts to a specific dimension, and takes a predetermined force to stretch the spring mechanism 120 incrementally beyond that dimension. In other embodiments, the spring mechanism 120 can be at least slightly open-wound, so that only a minimal force is generated for an incremental stretching of the spring. In these and other embodiments, the spring mechanism 120 may have other suitable structures that can contract or otherwise reduce in length and have sufficient strength to also contract the fixation member 102 and native tissue attached thereto. In certain embodiments, the spring mechanism 120 has a major diameter of 0.040 inch to 0.080 inch and a wire diameter of 0.06 inch to 0.016 inch.

The spring mechanism 120 can be sized such that it has a relaxed dimension that approximately corresponds to the length of the desired ultimate annular dimension. For example, if the spring mechanism 120 extends around the inferior circumference of the fixation member 102 as shown in FIG. 1A, the relaxed dimension of the spring mechanism 120 can correspond to the desired circumference of the annulus. The dimension can be selected based on the dimensions of a healthy annulus and/or the dimensions necessary to provide suitable leaflet prolapse.

Before implantation, when the spring mechanism 120 is affixed to or otherwise joined with the fixation member 102, the spring mechanism 120 can be held in a pre-stretched, extended state with a bioabsorbable material. The bioabsorbable material that retains the spring mechanism in its pre-stretched state can include PLA, PLGA, and/or other suitable bioabsorbable materials that dissolve over time within the body. When the spring mechanism 120 is a coil spring, this bioabsorbable material can be in the form of a thick thread or suture that is introduced into and extends through the central opening of the coil spring. This coaxial suture/spring arrangement is expected to allow a relatively small-diameter suture (e.g., 0.020-0.050 inch in diameter) to hold the spring mechanism 120 at an extended length in the pre-stretched state for the desired length of time. The overall length of the spring mechanism 120 in the pre-stretched state can be approximately the same as the corresponding dimension of the fixation member 102 in the expanded, deployed state. For example, in the embodiment shown in FIG. 1A, the length of the spring mechanism 120 in the pre-stretched state can correspond to the circumference of the distal end portion 104b of the fixation member 102 in the expanded state.

Figure 2A:
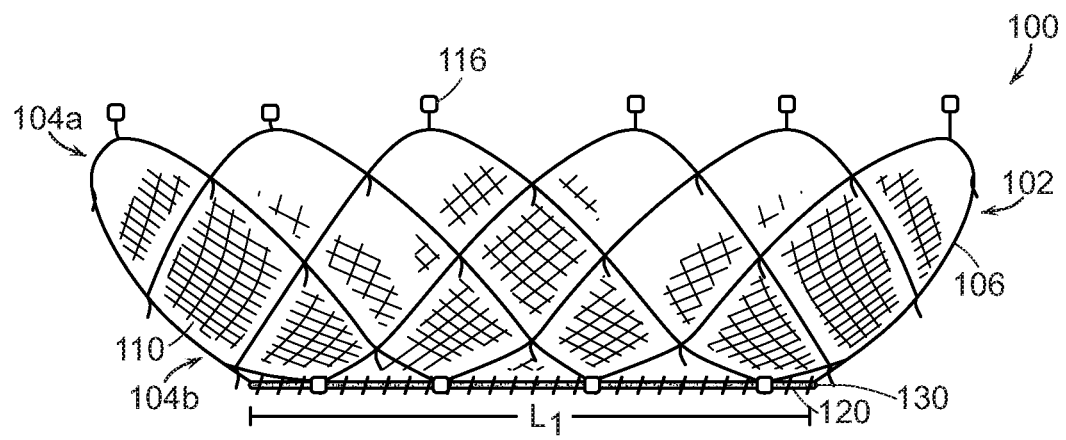
FIG. 2A is a side view of the mitral valve repair device of FIG. 1A in an initial, expanded state in accordance with embodiments of the present technology.
Figure 2B:
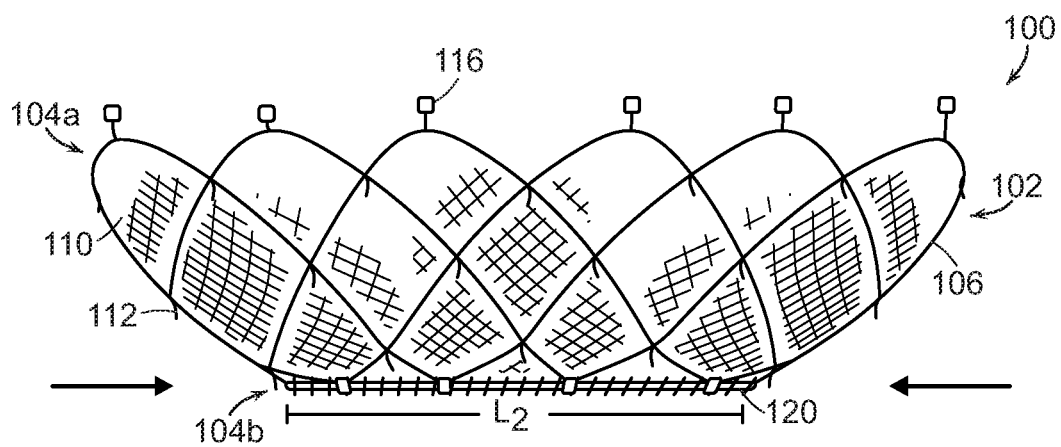
FIG. 2B is a side view of the mitral valve repair device of FIG. 1A in a contracted, relaxed state in accordance with embodiments of the present technology.

After the device 100 has been implanted and suitably anchored (e.g., via structural anchoring mechanisms 118 and/or tissue ingrowth) to the native tissue surrounding the annulus, the bioabsorbable material dissolves and causes the pre-stretched spring mechanism 120 to contract to its natural, relaxed state. Because the fixation member 102 is anchored to the adjacent cardiac tissue, this contraction of the spring mechanism 120 also draws the native annulus inward to reduce the overall dimensions of the native annulus, thereby re-establishing proper coaptation of the valve leaflets. This change from the initial pre-stretched state of the spring mechanism 120 to the contracted, relaxed state is illustrated in FIGS. 2A and 2B, respectively. More specifically, in the embodiment illustrated in FIG. 2A, the spring element 120 has a first length $L_1$ corresponding to an extended state and held in place with a bioabsorbable material 130 (e.g., a coating or suture). As shown in FIG. 2B, as the bioabsorbable material 130 dissolves, the spring element 120 is allowed to contract to a second length $L_2$, shorter than the first length $L_1$, corresponding to a natural, relaxed state. This contraction draws the annulus fixated to the fixation member 102 with it, thereby cinching the valve annulus to a desired dimension. Accordingly, the device 100 can reduce the dimensions of a dilated cardiac valve annulus, thereby moving native or prosthetic leaflets closer together again and allowing the leaflets (or a portion thereof) to coapt during systole. Further, in some patients, there may be reasons to believe that the mitral annulus is highly likely to dilate in the future. For these patients, a prophylactic annuloplasty device (e.g., the device 100 described above) that prevents that future dilation is also expected provide clinical benefits.

It should be noted that the native mitral valve can be a very stiff, fibrous structure, so that acutely changing its dimension requires significant force. Therefore, in a surgical annuloplasty procedure where the dimensions of the annulus are changed acutely, the ring exerting the force on the annulus must be very strong, and it must be very securely anchored to the annular tissue, typically by many sutures deeply embedded in the annular tissue. In contrast, if this annular contraction occurs over a period of months and millions of heartbeats, with an elastic spring member (e.g., the spring mechanism 120), the forces required to gradually reduce annular dimensions might be much lower. The associated tissue fixation forces required may similarly be much lower. Therefore, the healing of the fixation member 102 into the tissue, along with some barbs 112 or anchors 118 to enhance ingrowth into the tissue, are expected to be sufficient to prevent separation of the device 100 from the annulus.

The device 100 can also be used in conjunction with other devices, such as clips that join portions of leaflets together, a prosthetic leaflet device that provides for coaptation, a prosthetic valve device (e.g., serving as its landing pad or base), and/or other devices that provide for proper cardiac valve function.

Figure 3:
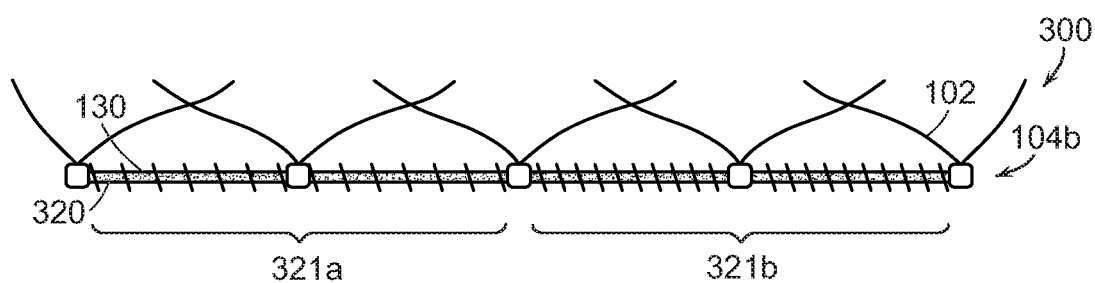
FIG. 3 is an enlarged view of an inferior edge portion of a mitral valve repair device configured in accordance with embodiments of the present technology.

FIG. 3 is an enlarged view of the inferior edge portion 104b of a mitral valve repair device 300 ("device 300") configured in accordance with embodiments of the present technology. The device 300 includes various features at least generally similar to the features of the devices 100 described above. For example, the device 300 include the fixation member 102 with at least one spring mechanism 320 configured to contract the inferior edge portion 104b of the fixation member 102. In the embodiment illustrated in FIG. 3, the spring mechanism 320 has varying degrees of pre-stretched extension along its length such that certain areas of the spring mechanism 320 are more pre-stretched than others. For example, as shown in FIG. 3, the spring mechanism 320 may have a first spring portion 321a that is held in a first pre-stretched state (e.g., via the biocompatible material 130) and a second spring portion 321b that is held in a second pre-stretched state, and the first pre-stretched state is such that the first spring portion 321a must undergo a greater degree of displacement (e.g., contraction) to return to its relaxed, normal state than the second spring portion 321b. The first and second spring portions 321a-b can be separate springs components or a single spring component, and each spring portion may have the same spring constant or the spring constants of the individual portions may differ. When the spring mechanism 320 is a loop placed circumferentially around the fixation member 102 (FIGS. 1A-3), the spring mechanism 320 can be stretched more near the commissures and the lateral and medial portions of the native mitral valve than at the portions that align with the anterior and posterior portions of the native mitral valve. In this configuration, contraction of the spring mechanism 320 is focused at the medial and lateral portions of the device 300, and thereby pulls the anterior and posterior portions of the native annulus toward each other to reduce the anterior-posterior dimension of the native. In some embodiments, the spring mechanism 320 can have a greater stretch in the portions that are aligned with the anterior and posterior portions of the native mitral valve to draw the medial and lateral sides of the native valve together. In some embodiments, the spring mechanism 320 can have differing degrees of contraction positioned elsewhere on the fixation member and/or with different orientations to the native anatomy to impart the desired degree of cinching of the native annulus and/or provide a desired end shape of the native annulus. Although FIG. 3 illustrates the spring mechanism 320 with two spring portions 321a-b having two different spring forces, valve repair devices disclosed herein can have more than two spring portions and/or more than two spring forces.

Figure 4:
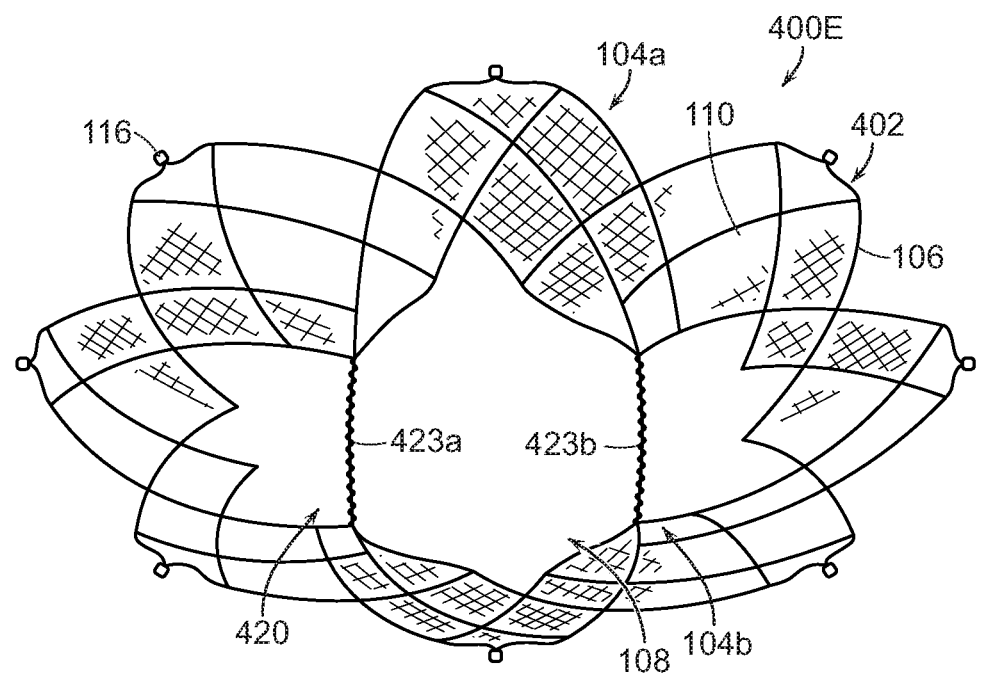
FIG. 4 is an isometric view of a mitral valve repair device configured in accordance with embodiments of the present technology.

FIG. 4 is an isometric view of a mitral valve repair device 400 ("device 400") configured in accordance with embodiments of the present technology. The device 400 includes numerous features generally similar to those of the device 100 described above with reference to FIGS. 1A-2B, such as a fixation member 402 and at least one spring mechanism 420 coupled to the inferior edge portion 104*b* of the fixation member 402. The fixation member 402 of FIG. 4, however, is preferentially ovalized with the anterior-posterior ("AP") as its major axis, which may result in little to no wall contact in the medial and lateral sides of the device 400 when implanted. In addition, the spring mechanism 420 extends across the central opening 108 of the fixation member 402, rather than around its circumference (e.g., as in FIGS. 1A-3). As shown in FIG. 4, the spring mechanism 420 can include a first spring component 423*a* spaced laterally apart from a second spring component 423*b* (referred to collectively as "spring components 423"), and the spring components 423 are attached to opposing sides of the inferior edge portion 104*b* of the fixation member 402 such that they span across the diameter or chord lengths of the inferior edge portion 104*b* of the fixation member 402. In this configuration, the length of the spring components 423 in the pre-stretched state can correspond to the diameter or corresponding chord length of the distal end portion 104*b* of the fixation member 402 in the deployed state (i.e., when not constrained by a delivery system), and the relaxed dimension of the spring mechanism 420 can correspond to the desired chord length or diameter at or near the native annulus. When the spring mechanism 420 moves from its pre-stretched to relaxed dimension (e.g., as the bioabsorbable material dissolves), the device 400 can gradually draw the native annulus inward based on the orientation and relaxed dimensions of the spring mechanism 420. For example, when the spring components 423 are positioned such that they extend between the posterior and anterior portions of the native annulus, the device 400 provides contraction of the native annulus in the AP direction to bring the anterior and posterior leaflets together, yet avoids causing additional or excessive expansion of the atrium in the commissure-commissure ("CC") direction.

In some embodiments, the spring mechanism 420 may have a single spring component spanning across the diameter or other chordal length of the fixation member 402, or the device 400 may include three or more spring components extending across the opening 108 of the fixation member 402. In some embodiments, the device 400 may include one or more spring components spanning across different portions of the fixation member 402 (e.g., across the superior portion 104*a* of the fixation member 402, across the medial wall of the fixation member 402, across the opening 108 from the superior portion 104*a* to the inferior portion 104*b*), the spring components may have variable spring forces in the pre-stretched state, and/or the spring components may draw in the native annulus and/or other cardiac tissue attached to the fixation member 402 in different directions (e.g., the CC direction).

Figure 5A:
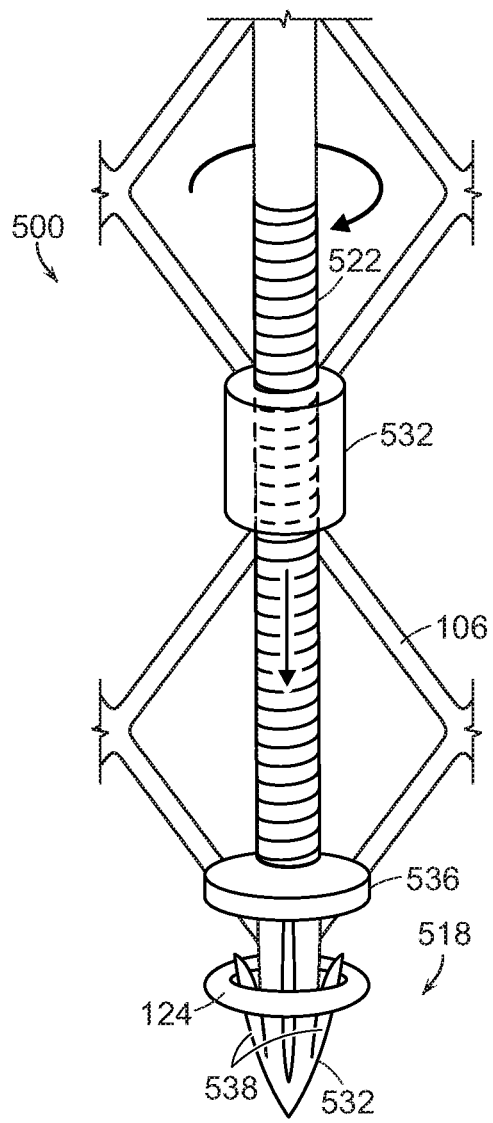
FIGS. 5A and 5B are enlarged views of a tissue anchoring element of a mitral valve repair device in a delivery state and a deployed state, respectively, configured in accordance with embodiments of the present technology.
Figure 5B:
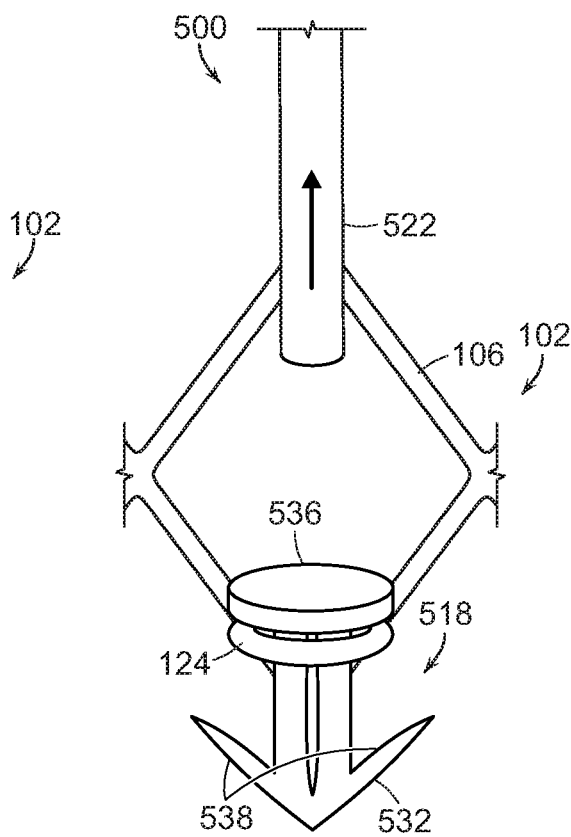

FIGS. 5A and 5B are enlarged views of a tissue anchoring element 518 of a mitral valve repair device 500 ("device 500") in a delivery state and a deployed state, respectively, configured in accordance with embodiments of the present technology. The device 500 can include features generally similar to the features of the devices 100, 300, 400 described above with respect to FIGS. 1A-4. For example, the device 500 includes the fixation member 102 and one or more anchoring elements 518 that engage cardiac tissue proximate to the inferior edge portion 104*b* of the fixation member 102, thereby enhancing device fixation. Unlike the helical coil anchor 126 illustrated in FIGS. 1B and 1C, the anchoring element 518 of the device 500 is a hook anchor 532 that can be coupled to eyelets 124 and/or other connection structures along the fixation member 102. The hook anchor 532 can be driven into the tissue using a shaft 522 acting on a portion (e.g., a flange 536) of the hook anchor 532. For example, as shown in FIG. 5A, the shaft 522 can extend through a guide 534 on the fixation member 102 aligned with the eyelet 124, and a shaft 522 can be rotated and/or translated longitudinally within the guide 534 to move the hook anchor into the tissue. As the hook anchor 532 is driven through the eyelet 124, the pressure from the eyelet 124 can fold barbs 538 of the hook anchor 532 inward (FIG. 5A). Once through the eyelet, the barbs 538 can pop radially outward to engage the underlying tissue while the flange 536 extends over the eyelet 124 to maintain engagement with the fixation member 102 (FIG. 5B). In some embodiments, the hook anchor 532 may have different features and/or be deployed via other mechanisms including self-deployment.

Figure 6A:
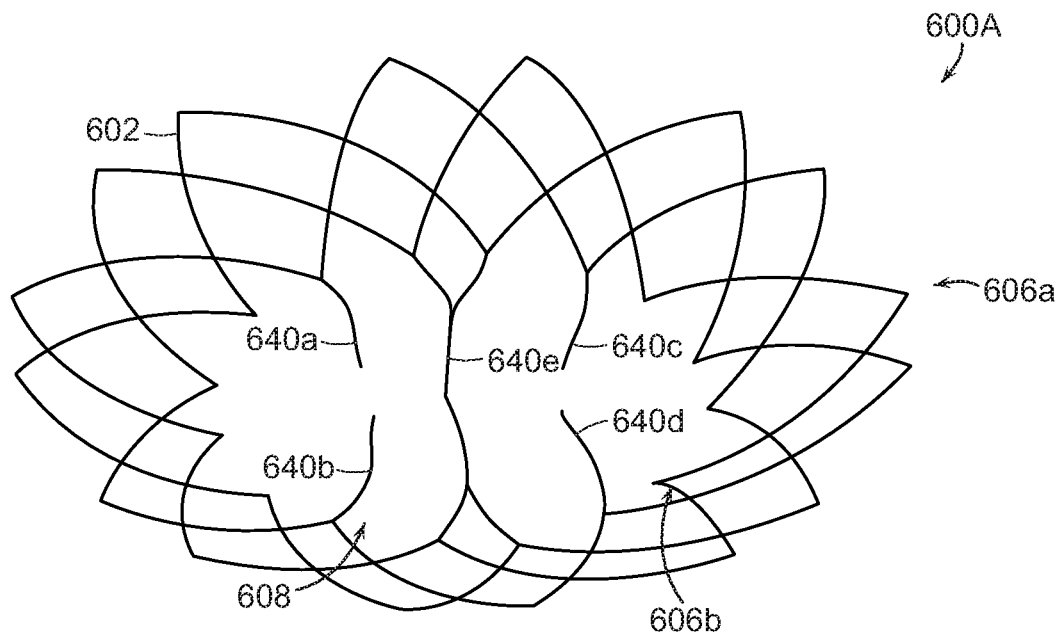
FIG. 6A illustrates a mitral valve repair device configured in accordance with additional embodiments of the present technology.
Figure 6B:
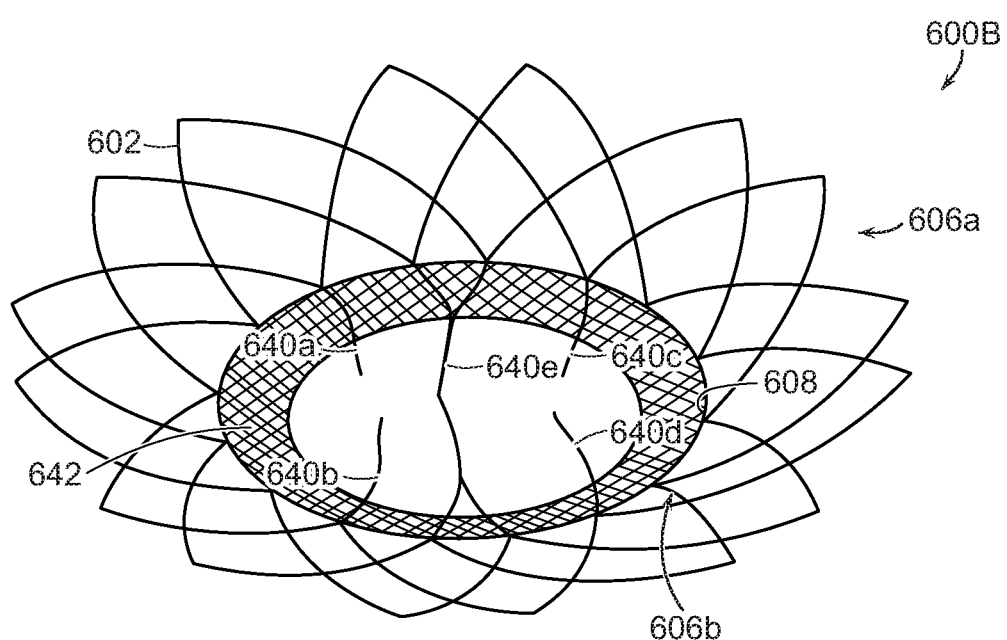
FIG. 6B illustrates a mitral valve repair device configured in accordance with additional embodiments of the present technology.

In various embodiments, mitral valve repair devices disclosed herein can include additional elements to enhance their ability to restore competence to the native valve. FIGS. 6A and 6B, for example, illustrate annuloplasty devices 600A and 600B, respectively, (referred to collectively as "devices 600") configured in accordance with additional embodiments of the present technology. The devices 600 can include various features at least generally similar to the features of the devices 100, 300, 400 and 500 described above with reference to FIGS. 1A-5B. For example, the devices 600 include a fixation member 602 and one or more spring mechanisms (not shown) configured to contract the inferior edge portion 604*b* of the fixation member 602. As shown in FIG. 6A, the annuloplasty device 600A can further incorporate one, two, or more wires or arms (identified individually as first through fifth arms 640*a-e*, respectively; referred to collectively as "arms 640") extending across at least a portion of the opening 608 of the fixation member 602 to limit prolapse of the valve leaflets. These arms 640 can extend radially inward and/or distally (e.g., towards the left ventricle) from the distal edge portion 604*b* of the fixation member 602 near the annulus. The arms 640 can each be independent from one another or adjacent arms 640 may be connected to each other. In some embodiments, one or more of the arms 640 (e.g., the fifth arm 640*e*) may extend completely across the central opening 608 of the device 600A (i.e., across the native annulus when implanted), or two arms 640 extending from opposing sides of the fixation member 602 can be connected to each other to extend across the opening 608. In these embodiments, the arms 640 may initially extend fairly directly across the central device opening 608, and then as the contraction of the device 600 decreases the native annulus diameter over time, the arms 640 may bend further away from the fixation member 602 in a distal direction towards the ventricle. The connected arms 640 that extend across the opening 608 of the device 600 may also have features (e.g., scoring, perforations) that creates a weakened region to allow the arm(s) 640 to break apart and separate if it is desired when a predetermined force is imparted thereon (e.g., to place a prosthetic replacement valve at a later time).

As shown in FIG. 6B, in some embodiments the proximal section of the arms 640 may be joined together by a skirt or hem 642 of fabric (e.g., ePTFE) or tissue to encourage ingrowth at the base of the native leaflets and to provide an atraumatic surface for the native leaflets. This fabric hem 642 might also enhance sealing in regions with less native leaflet tissue such as the commissures and the clefts. The distal ends of the arms 640 may also be covered in fabric or tissue to provide an atraumatic surface (not shown).

Figure 7:
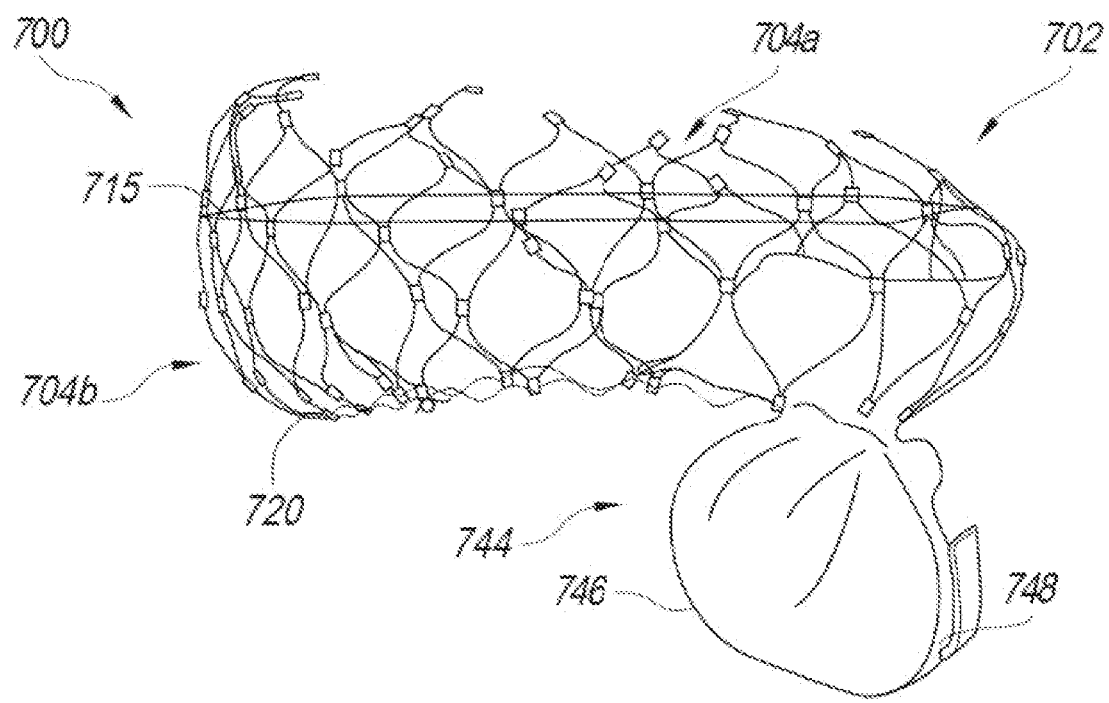
FIG. 7 is a side view of a cardiac valve repair device configured in accordance with some embodiments of the present technology.

In some embodiments, the devices disclosed herein can include structural features that assist coaptation of the native leaflets. FIG. 7, for example, illustrates a cardiac valve repair device 700 ("device 700") configured in accordance with some embodiments of the present technology. The device 700 includes various features at least generally similar to the features of the devices 100, 300, 400, 500 and 600 described above with reference to FIGS. 1A-6B. For example, the device 700 includes an atrial fixation member 702 with a superior edge portion 704a and an inferior mesh portion 704b and one or more spring mechanisms 720 configured to contract the inferior edge portion 704b of the fixation member 702. The fixation member 702 can include a mesh frame 706 with an optional suture ring 715 extending therearound to facilitate deployment, recapture, and/or cinching of the fixation member 702 after tissue ingrowth. As shown in FIG. 7, the device 700 further includes a coaptation structure 744 (also referred to as a "baffle" or "coaptation member") extending in a distal direction away from the inferior edge portion 704b of the fixation member 702 and radially inward from the fixation member 702 into a central lumen 708 such that the coaptation structure 744 is configured to occlude a portion of the native valve orifice. The coaptation structure 744 has an anterior surface 746 configured to coapt with at least a portion of a first native leaflet during systole and a posterior surface 748 configured to displace at least a portion of a second native leaflet. For example, when implanted within the mitral valve, the coaptation structure 744 can be positioned in front of the P2 portion of the posterior leaflet to provide an anterior coaptation surface 746 for the anterior leaflet. In various embodiments, the coaptation structure 744 is substantially stationary (little to no movement, unlike a native leaflet) during cardiac cycles. In some embodiments, the coaptation structure 744 moves during cardiac cycles similar to a native leaflet.

Suitable baffle structures are disclosed in PCT Patent Application No. PCT/US2018/043566, filed Jul. 24, 2018, entitled PROSTHETIC LEAFLET DEVICE. In these and other embodiments, the devices disclosed herein can incorporate one or more different space-filling elements suspended from the fixation member to occlude a portion of the valve orifice which is not occluded by the native leaflets. For example, the devices may include a tongue-shaped inflatable element connected to the fixation member at the commissures of the valve. In other embodiments, the device can include different types of space filling elements extending from the fixation member to facilitate coaptation.

In various embodiments, the device can serve as a ring or base for future placement of a prosthetic replacement valve into the annulus. This device would have an appropriate final size (i.e., when the spring element is in its relaxed state) and spring strength to adequately retain a prosthetic valve disposed therein. This device can also be combined with minimally invasive edge to edge repair for durable long-term reduction of mitral valve regurgitation.

The annuloplasty devices disclosed herein can be delivered via a variety of catheter-based approaches from the femoral vein, femoral artery, etc. to access the native mitral valve. A tricuspid version of the device could be delivered from the jugular vein. The devices can also be delivered via minimally-invasive-surgical trans-apical or trans-atrial approaches, or via open surgical placement. For delivery, the spring element(s) can be folded distally of the fixation member so as not to increase the overall diameter of the device in the delivery state. The spring element(s) and/or the bioabsorbable material can also be shaped so that the sections between the attachment points to the fixation member naturally fold distally (away from the interior of the fixation member) when the device is collapsed to aid in packing for delivery and/or retrieval.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A mitral valve repair device comprising:
   an atrial fixation member configured to engage tissue within a left atrium proximate to a native mitral valve annulus, the atrial fixation member comprising—
     a superior edge portion configured to be positioned within the atrium spaced apart from the native mitral annulus and having a superior edge portion diameter,
     an inferior edge portion configured to be positioned proximate to the native mitral annulus and having an inferior edge portion diameter,
     wherein the atrial fixation member is configured to expand from a delivery state to a deployed state, and wherein the inferior edge portion diameter is configured to be less than the superior edge in the deployed state; and a spring mechanism coupled to the inferior edge portion, wherein— the spring mechanism has an extended state with a first length corresponding to a dimension of the atrial fixation member in the deployed state and a relaxed state with a second length shorter than the first length, the spring mechanism (i) being in the extended state when the atrial fixation member is in the deployed state and (ii) including a bioabsorbable material on at least a portion of the spring mechanism maintaining the spring mechanism at least partially in the extended state, and when implanted, the bioabsorbable material is configured to dissolve and allow the spring mechanism to approach the relaxed state and contract the inferior edge portion of the atrial fixation member such that the native mitral annulus anchored to the atrial fixation member reduces in a cross-sectional dimension.

2. The mitral valve repair device of claim 1 wherein the spring mechanism encircles a perimeter of the inferior edge portion of the fixation member.

3. The mitral valve repair device of claim 1 wherein:
the atrial fixation member defines a central lumen extending therethrough; and
the spring mechanism extends between opposing sides of the atrial fixation member across the central lumen.

4. The mitral valve repair device of claim 1 wherein the spring mechanism comprises:
a first spring portion retained in a first pre-stretched state having a first spring force; and
a second spring portion retained in a second pre-stretched state having a second spring force different than the first spring force.

5. The mitral valve repair device of claim 1 wherein the atrial fixation member comprises a mesh frame that defines a central lumen configured to allow blood to pass therethrough.

6. The mitral valve repair device of claim 5, further comprising a covering extending over at least a portion of the mesh frame.

7. The mitral valve repair device of claim 5, further comprising a plurality of cleats projecting outwardly from the mesh frame, wherein the cleats are configured to enhance tissue fixation.

8. The mitral valve repair device of claim 1, further comprising a plurality of anchoring elements along the inferior edge portion of the atrial fixation member, wherein the anchoring elements are configured to engage tissue proximate to the native mitral valve annulus after the fixation member has been positioned against an atrial wall.

9. The mitral valve repair device of claim 8 wherein:
the atrial fixation member comprises a plurality of eyelets along the inferior edge portion; and
the anchoring elements are helical coil anchors configured to extend through the eyelets.

10. The mitral valve repair device of claim 8 wherein:
the atrial fixation member comprises a plurality of eyelets along the inferior edge portion; and
the anchoring elements are hook anchors configured to extend through the eyelets.

11. The mitral valve repair device of claim 1 wherein the atrial fixation member comprises a nitride-based nanomatrix coating to facilitate tissue ingrowth.

12. The mitral valve repair device of claim 1 wherein the atrial fixation member comprises a mesh frame having an oval shape with a major axis configured to be oriented between an anterior wall of the left atrium and a posterior wall of the left atrium.

13. The mitral valve repair device of claim 1, further comprising delivery attachment features positioned along the superior edge portion of the atrial fixation member and configured to facilitate connection to a delivery device.

14. The mitral valve repair device of claim 1 wherein:
the atrial fixation member defines a central lumen configured to allow blood to pass therethrough; and
the mitral valve repair device further comprises a plurality of arms extending across at least a portion of the central lumen to limit prolapse of native valve leaflets.

15. The mitral valve repair device of claim 14, further comprising a skirt extending from the inferior edge portion inwardly toward the central lumen and positioned between the arms, wherein the skirt is configured to promote tissue ingrowth with the native valve leaflets.

16. The mitral valve repair device of claim 14 wherein at least one of the plurality of arms extends completely across the central lumen, and wherein contraction of the spring mechanism causes the at least one of the plurality of arms to bend away from the atrial fixation member in a direction away from the superior edge portion.

17. The mitral valve repair device of claim 1 wherein:
the atrial fixation member defines a central lumen configured to allow blood to pass therethrough;
the mitral valve repair device further comprises at least one arm extending completely across the central lumen to limit prolapse of valve leaflets; and
the arm has a weakened region configured to break apart when a predetermined force is imparted onto the weakened region.

18. The mitral valve repair device of claim 1, further comprising a suture ring extending around a circumference of the atrial fixation member and configured to be tightened to decrease a cross-sectional area of the atrial fixation member.

19. The mitral valve repair device of claim 1, further comprising a coaptation structure extending away from the atrial fixation member and radially inward from the atrial fixation member, the coaptation structure comprising:
an anterior surface configured to coapt with a first native leaflet during systole; and
a posterior surface configured to displace at least a portion of a second native leaflet,
wherein the coaptation structure is substantially stationary during cardiac cycles.

20. A cardiac valve repair device comprising:
a fixation member configured to engage cardiac tissue in a chamber of a heart proximate to a native valve annulus, the fixation member comprising—
a mesh frame defining a central lumen extending therethrough,
a proximal edge portion configured to be spaced apart from the native annulus and having a proximal edge portion diameter, and
a distal edge portion configured to be positioned proximate to the native annulus and having a distal edge portion diameter, wherein the distal edge portion diameter is configured to be less than the proximal edge portion diameter in the deployed state;
a spring mechanism coupled to the distal edge portion, wherein the spring mechanism has a pre-stretched state with a first length and a relaxed state with a second length shorter than the first length;

a bioabsorbable material on at least a portion of the spring mechanism, the bioabsorbable material being configured to maintain the spring mechanism at least partially in the pre-stretched state when the fixation member is deployed, wherein the bioabsorbable material is further configured to dissolve over time to delay movement of the spring mechanism from the pre-stretched state to the relaxed state; and when the spring mechanism moves to the relaxed state, the spring mechanism draws the distal edge portion radially inward to reduce dimensions of the fixation member such that the native annulus anchored to the fixation member reduces in a cross-sectional dimension.

21. The cardiac valve repair device of claim 20 wherein the spring mechanism extends around a circumference of the distal edge portion.

22. The cardiac valve repair device of claim 20 wherein the spring mechanism comprises at least one spring component extending across a chordal length of the central lumen.

23. The cardiac valve repair device of claim 20 wherein the spring mechanism comprises:

a first spring portion having a first spring force in the pre-stretched state; and a second spring portion having a second spring force in the pre-stretched state, the first spring force being different than the second spring force.

24. The cardiac valve repair device of claim 20, further comprising:

a covering extending over at least a portion of the mesh frame; and a plurality of cleats projecting outwardly from the mesh frame, wherein the cleats are configured to enhance tissue fixation.

25. The cardiac valve repair device of claim 20, further comprising a plurality of anchoring elements along the distal edge portion of the fixation member, wherein the anchoring elements are configured to engage tissue proximate to the native valve annulus.

26. The cardiac valve repair device of claim 25 wherein the plurality of anchoring elements comprises three anchoring members configured to align with trigones and a P2 region of the native valve annulus.

27. The cardiac valve repair device of claim 20, further comprising a plurality of arms extending across at least a portion of the central lumen to limit prolapse of valve leaflets.

28. A cardiac valve repair device comprising:

a fixation member configured to engage cardiac tissue in a chamber of a heart proximate to a native valve annulus, the fixation member comprising— a mesh frame defining a central lumen extending therethrough, a proximal edge portion configured to be spaced apart from the native annulus and having a proximal edge portion diameter, and a distal edge portion configured to be positioned proximate to the native annulus and having a distal edge portion diameter, wherein the distal edge portion diameter is configured to be less than the proximal edge portion diameter in the deployed state;

a spring mechanism coupled to the distal edge portion, wherein the spring mechanism has a pre-stretched state with a first length when the fixation member is initially deployed and a relaxed state with a second length shorter than the first length;

a bioabsorbable material on at least a portion of the spring mechanism, the bioabsorbable material being configured to (i) maintain the spring mechanism at least partially in the pre-stretched state after the fixation member is deployed, and (ii) dissolve to allow for a time delayed contraction of the spring mechanism to the relaxed state; and when the spring mechanism moves to the relaxed state, the spring mechanism draws the distal edge portion radially inward to reduce dimensions of the central lumen at the distal edge portion of the fixation member.

* * * * *